United States Patent [19]
Jay et al.

[11] Patent Number: 6,074,674
[45] Date of Patent: Jun. 13, 2000

[54] FORMULATIONS FOR SUSTAINED-RELEASE OF TOPICAL ANESTHETICS AND METHODS OF MAKING AND USING SAME

[75] Inventors: Michael Joseph Jay; G. Thomas Kluemper; Sang Hun Kim, all of Lexington, Ky.

[73] Assignee: University of Kentucky Research Foundation, Lexington, Ky.

[21] Appl. No.: 09/119,099

[22] Filed: Jul. 20, 1998

Related U.S. Application Data

[60] Provisional application No. 60/063,904, Oct. 31, 1997.

[51] Int. Cl.⁷ ..................................................... A61K 9/50
[52] U.S. Cl. ........................ 424/502; 424/484; 424/485; 424/486; 424/78.02; 424/78.03; 514/817; 514/900; 514/902
[58] Field of Search ..................................... 424/484, 485, 424/486, 502, 78.02, 78.03; 514/817, 900, 902

[56] References Cited

U.S. PATENT DOCUMENTS

| | | | |
|---|---|---|---|
| 4,740,365 | 4/1988 | Yukimatsu et al. | 424/435 |
| 4,834,985 | 5/1989 | Elger et al. | 424/488 |
| 4,952,560 | 8/1990 | Kigasawa et al. | 514/2 |
| 5,288,497 | 2/1994 | Stanley et al. | 424/440 |
| 5,362,737 | 11/1994 | Vora et al. | 514/291 |
| 5,451,409 | 9/1995 | Rencher et al. | 424/468 |

OTHER PUBLICATIONS

Schroeder, et al., 67(3) *J. Pharm. Sci.* (1978), 350–353.
Dakkuri, et al., 67(3) *J. Pharm. Sci.* (1978), 354–357.
Dakkuri, et al., 67(3) *J. Pharm. Sci.* (1978), 357–360.
Kotsiomiti & McCabe, 23 *J. Oral Rehabil.* (1996), 114–120.
McCabe, J.F., *Applied Dental Materials* (7th ed.) (Blackwell Scientific Publications, Oxford), 34–37, 1986.
McCrorie, 1 *J. Oral Rehab.* 29 (1974), pp. 29–45.
DRUGU AN 98–25468, Kim et al., Pharm. Res., 14, No. 11, Suppl., S42, 1997.
DRUGU, AN 90–40921, Ismail et al., *Sci. Tech. Prat. Pharm.* (6, No. 6, 380–87, 1990).

*Primary Examiner*—Dwayne C. Jones
*Assistant Examiner*—C. Delacroix-Muirheid
*Attorney, Agent, or Firm*—Kristine H. Johnson; Macheledt Bales & Johnson LLP

[57] ABSTRACT

The present invention provides, inter alia, formulations useful to ameliorate symptoms associated with mucosal abrasions, specifically those due to dental orthodontic brackets; oral surgery; periodontal surgery or other procedures. For instance, there is a formulation comprising: 65 to 75% microcrystalline wax; 5 to 15% non-ionic polymer; 15 to 25% topical anesthetic; and 1 to 5% surfactant, wherein the ratio of non-ionic polymer to microcrystalline wax is no greater than 0.2. Preferably, for solid topical anesthetics, the particle size is less than the apertures of a 100-mesh screen. However, the topical anesthetic may also be a liquid. Formulations wherein the mixture is a homogeneous matrix is preferred.

21 Claims, 4 Drawing Sheets

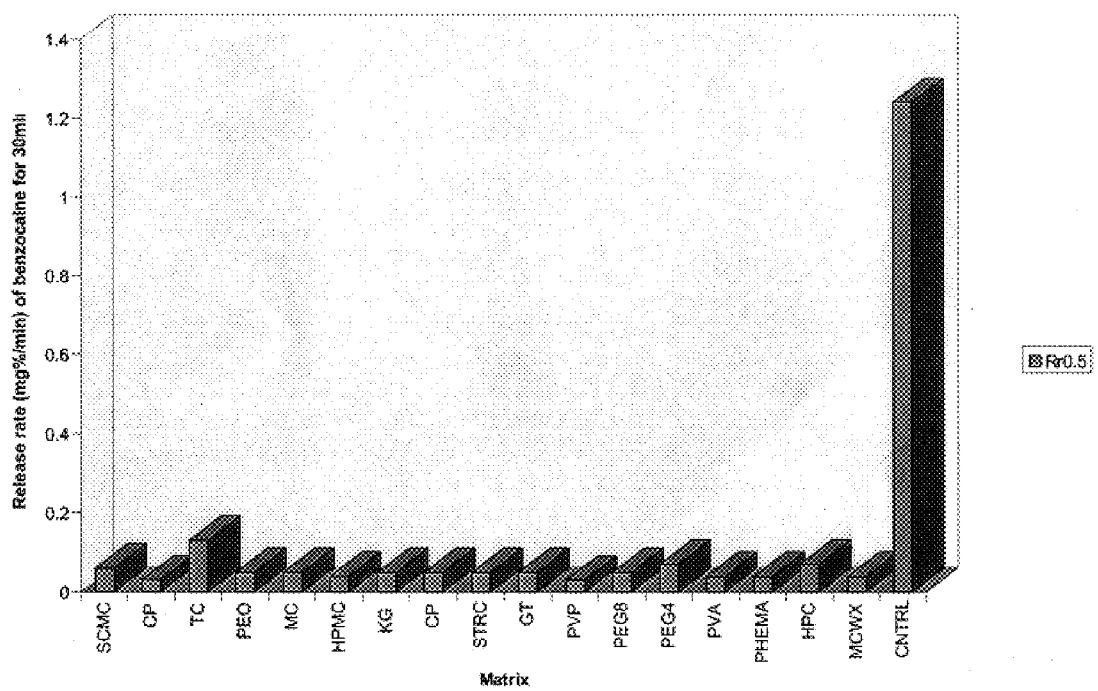
Fig. 1. Comparison of release rate of benzocaine (Rr0.5) for 30 min in several matrices.

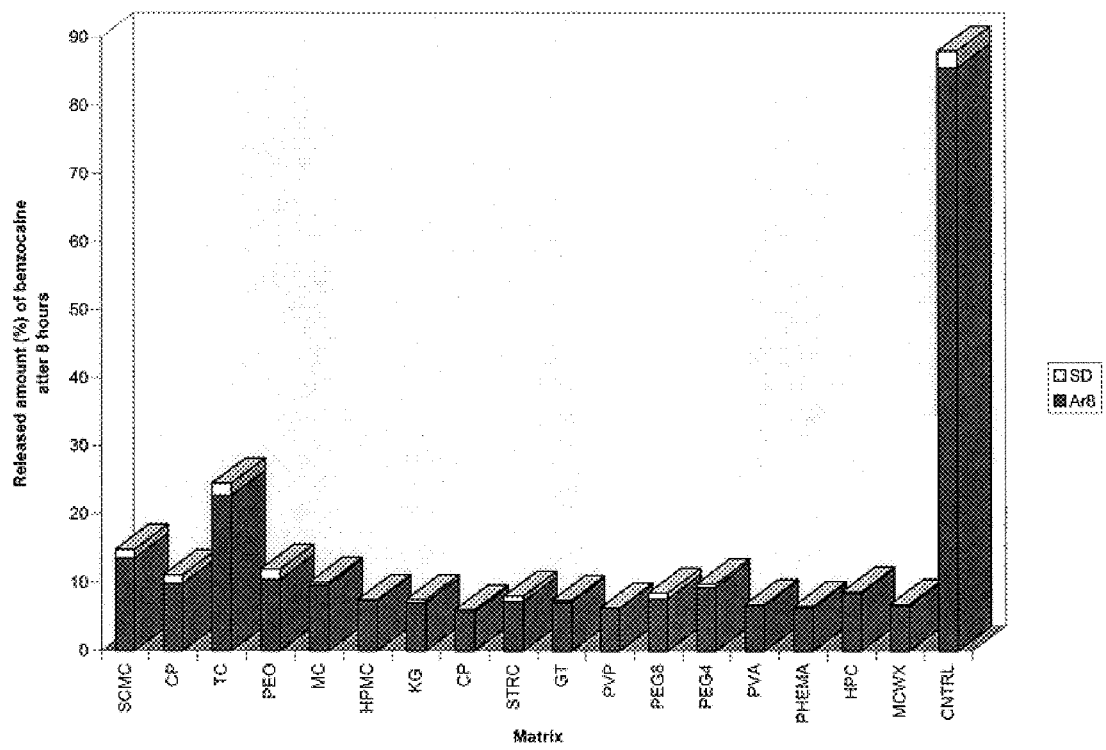
Fig. 2. Comparison of released amount of benzocaine after 8 hours (Ar8) for several polymer/wax matrices.

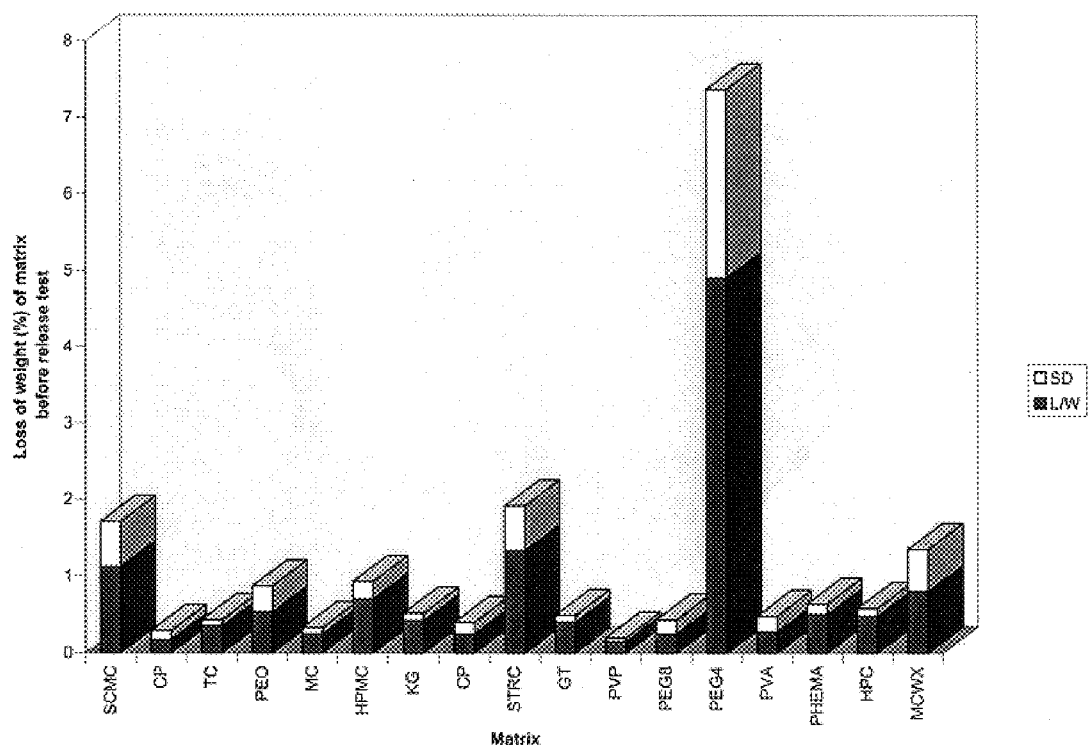
Fig. 3. Comparison of loss of weight (L/W) for several polymer/wax matrices.

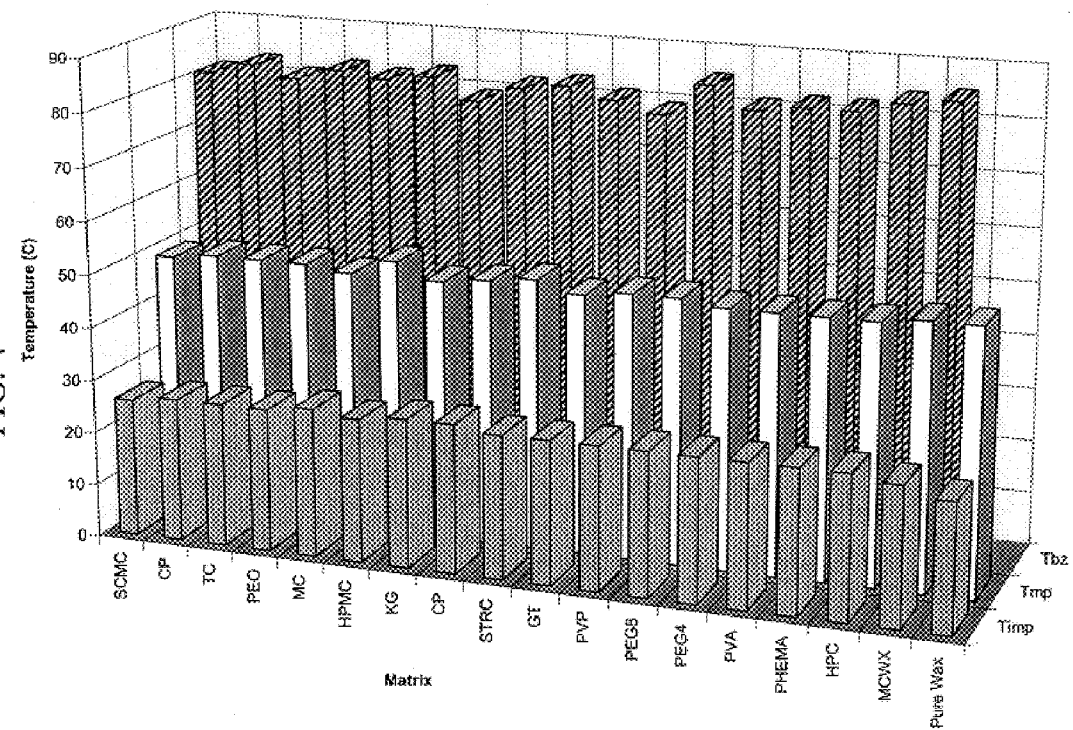
Fig. 4. Comparison of initial melting point (T$imp$, °C), melting point (T$mp$, °C) of matrices and melting point of benzocaine (T$bz$, °C).

FORMULATIONS FOR SUSTAINED-RELEASE OF TOPICAL ANESTHETICS AND METHODS OF MAKING AND USING SAME

This Application claims priority to Provisional Patent Application No. 60/063,904, filed Oct. 31, 1997.

BACKGROUND OF THE INVENTION

Orthodontic patients who require corrective braces almost always develop mouth abrasions due to friction between the orthodontic brackets and the oral mucosa. Previous treatments have included the use of wax to cover the brackets, and the use of topical anesthetics to treat the wounds.

Currently, dental wax is used by most, if not all, orthodontic patients to treat the problem of mouth abrasions. Typically, soft wax is applied to the brackets to reduce the friction. This is done on a prophylactic or as-needed basis and is often used in conjunction with a topical anesthetic that is applied directly to the irritated mucosa.

Topical anesthetic formulations to date have proved transitory in action; that is, the effect lasts for a matter of minutes. The fleeting action is due to the water soluble nature of the topical anesthetics, and the water-rich environment into which they are introduced.

One patent, U.S. Pat. No. 4,740,365 describes a preparation which provides sustained release of pharmaceuticals (including benzocaine) via a layered copolymer. Use of this film on dental brackets is inappropriate, for structural reasons, nor would it solve the unique problems of dental bracket abrasions.

Moreover, waxes and wax/polymer/surfactant formulations have been used in dentistry for the purpose of making impressions of a patient's teeth. Waxes may be then used as a mold for casting artificial teeth or for diagnostic purposes. Previous wax formulations of this sort did not incorporate an anesthetic, since the use did not warrant such incorporation.

The waxes used in dentistry normally consist of two or more components which may be natural or synthetic waxes, resins, oils, fats and pigments. Blending is carried out to produce a material with the required properties for a specific application. J. F. McCabe. Applied dental materials (7th ed.). Blackwell Scientific Publications, Oxford. Waxes are thermoplastic materials which are normally solids at room temperature but melt, without decomposition, to form mobile liquids. They are, essentially, soft substances with poor mechanical properties and their primary uses in dentistry are to form patterns of appliances prior to casting. An important group of waxes used in dentistry are the impression waxes. Waxes are generally characterized by their thermal properties such as melting point and solid-solid transition temperature which is closely related to the softening temperature observed in practice. Important mechanical properties are brittleness and the degree of flow which a material will undergo in its working temperature range. See, for example, Kotsiomiti & McCabe, 23 *J. Oral Rehabil.* 114 (1996).

In McCrorie, 29 *J. Oral Rehab.* 29 (1974), there is a review of the sparse information known prior to this publication regarding modelling waxes, and some objective data for several known modelling waxes. The paper compares the modelling waxes to ordinary waxes, such as paraffins and beeswaxes. The author gives his suggestions (on page 44) to those who are trying to identify useful modelling waxes.

In Lolor et al., 84(6), *J. Pharm. Sci.* 673 (1995), there is disclosed a study of factors desirable in a transdermal preparation. Lolor deals primarily with water/oil/surfactant preparations, and does not discuss wax embodiments.

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

It is therefore an object of the present invention to provide formulations useful to treat mucosal abrasions.

It is a further object to provide a method for making formulations to treat mucosal abrasions.

It is yet another object to provide methods to treat mucosal abrasions.

It is yet another object to provide methods to reduce pain due to mucosal abrasions.

Definitions: For the purposes of the present application, the following terms shall have the meanings as described below. All other terms shall have the meanings commonly recognized in the art at the time of filing.

"Non-ionic polymer(s)" shall mean non-ionic polymer(s) that are hydrophilic or lipophilic.

BRIEF DESCRIPTION OF THE DRAWINGS

FIG. 1 is a bar graph showing the comparison of release rate of benzocaine for 30 minutes in several matrices.

FIG. 2 is a bar graph showing the released amount of benzocaine after 8 hours for several polymer/wax matrices.

FIG. 3 is a bar graph showing the comparison of loss of weight for several polymer/wax matrices.

FIG. 4 is a comparison of initial melting point, melting point of matrices and melting point of benzocaine.

DETAILED DESCRIPTION OF THE INVENTION

The present invention therefore provides, inter alia, formulations useful to ameliorate symptoms associated with mucosal abrasions, specifically those due to dental orthodontic brackets; oral surgery; periodontal surgery or other procedures. For instance, there is a formulation comprising: 65 to 75% microcrystalline wax; 5 to 15% non-ionic polymer; 15 to 25% topical anesthetic; and 1 to 5% surfactant, wherein the ratio of non-ionic polymer to microcrystalline wax is no greater than 0.2. Preferably, for solid topical anesthetics, the particle size is less than the apertures of a 100-mesh screen. However, the topical anesthetic may also be a liquid. Formulations wherein the mixture is a homogeneous matrix is preferred.

Specifically provided is a formulation as above, wherein the microcrystalline wax, non-ionic polymer and topical anesthetic are prepared according to the methods described herein.

Preferred formulations are those wherein the topical anesthetic is selected from the group consisting of: benzocaine; lidocaine; novocaine; procaine; butalaine; and dyclonine. Also preferred are those formulations wherein the non-ionic polymer is selected from the group consisting of: sodium carboxymethyl cellulose; Carbopol ETD 2001 resin; tragacanth; poly (ethylene oxide); methylcellulose; hydroxypropylmethylcellulose; karya gum; cellulose; soluble starch; gelatin; poly (vinyl pyrrolidone); poly (ethylene glycol)

8000; poly (ethylene glycol) 4000; and poly (vinyl alcohol). Formulations wherein the surfactant is selected from the group consisting of: sorbitan monolaurate, polysorbate 80 Spans and Tweens are also preferred.

A formulation wherein the topical anesthetic is benzocaine is herein provided. A formulation wherein the topical anesthetic is benzocaine, and the non-ionic polymer is tragacanth is more preferred. A formulation wherein the topical anesthetic is benzocaine, the non-ionic polymer is tragacanth, and the surfactant is Span80 is most preferred. Specifically, a formulation wherein, of the total, the tragacanth is 7.1%, the microcrystalline wax is 70.9%, the Span80 is 2.0% and the benzocaine is 20.0% is provided. However, formulations which comprise liquid anesthetics are also provided.

In making the above formulations, it is desirable to make a uniform matrix. The wax/polymer/surfactant mixture can be made according to means known in the art of making waxes. For example, the references cited in the background section of this application will be useful. For instance, the polymer to wax ratio may be up to 0.2. The methods described herein result in the proper physical parameters, and can also be used to manufacture the above formulations.

The present invention also provides methods to prepare formulations useful to treat symptoms associated with dental abrasions. Specifically, there are provided methods comprising the steps of: adding a topical anesthetic with particle size less than the apertures in a 100 mesh screen to a homogeneous mixture of melted microcrystalline wax, non-ionic polymer and surfactant, in a plurality of portions and with mixing, so as to obtain a homogenous mixture of said anesthetic, wax, polymer and surfactant; and cooling said homogenous mixture of said anesthetic, wax, polymer and surfactant at a constant rate, with continuous agitation, so as to congeal the mixture into a homogeneous matrix.

By "homogeneous mixture" and "homogeneous matrix" it is meant that every sample of the mixture or matrix is of similar composition, that is, the ratio of components is the same, for like sample sizes.

Alternatively, the formulations of the present invention can be manufactured as follows: Wax can be added to a manufacturing kettle with heating/cooling capabilities. The kettle should also be equipped with a bottom-to top recirculating pump and a mixer with a shaft and blade. The wax should be heated to approximately 65 to 70° C. The polymer and surfactant should be individually followed by the anesthetic. Then, the mixing process should be continued until all material is in a homogeneous state. The mixture should be gradually cooled (approximately 1° C. ° C./minute) and the cooled materials filtered using the re-circulation pump, into a clean receiving tank. The materials are optimally retained at a moldable consistency for further processing, testing or dispensing. Then, the materials are transfered for dispensing.

Topical anesthetics used in the present methods can be any molecules which provide pain relief for the oral mucosa. In a specific embodiment, the topical anesthetic can be, for example, benzocaine; lidocaine; novocaine; procaine; butalaine; and dyclonine.

Non-ionic polymers used in the present methods can be any molecules which are without electrical charge, that is, they are neutral. In a specific embodiment, the non-ionic polymer can be, for example: sodium carboxymethyl cellulose; Carbopol ETD 2001 resin; tragacanth; poly (ethylene oxide); methylcellulose; hydroxypropylmethylcellulose; karya gum; cellulose; soluble starch; gelatin; poly (vinyl pyrrolidone); poly (ethylene glycol) 8000; poly (ethylene glycol) 4000; and poly (vinyl alcohol).

In a preferred embodiment of the present invention, there is provided a method wherein the microcrystalline wax is first melted 65–70° C.; the polymer and surfactant are subsequently added with stirring; the sieve-shaker-screened benzocaine is subsequently added with stirring so as to produce a mixture; the mixture then stired for 5 to 10 minutes at 65 to 70° C.; the mixture then cooled with constant manual mixing so as to form a solid with a homogeneous matrix. The solid homogeneous matrix may then optionally be formed into uniform pieces of a size appropriate to place on individual dental brackets.

In another preferred embodiment, there is provided a method wherein the topical anesthetic is benzocaine. A method wherein the anesthetic is benzocaine and the non-ionic polymer is tragacanth is specifically preferred. More preferred is a method wherein the anesthetic is benzocaine, the non-ionic polymer is tragacanth and the surfactant is Span80. Most preferred is method wherein, of the total the tragacanth is 7.1%, the microcrystalline wax is 70.9%, the Span80 is 2.0% and the benzocaine is 20.0%.

Also provided are methods of reducing pain due mucosal abrasions in a patient in need of such pain reduction, comprising administering a formulation as described above. Specifically, methods of reducing pain due to mucosal abrasions in a patient in need of such pain reduction, comprising administering a formulation wherein the topical anesthetic is benzocaine, the non-ionic polymer is tragacanth, and the surfactant is Span 80 is most preferred.

EXAMPLES

Example 1

Optimizaton of Sustained Release of Benzocaine from Tragacanth/Wax/Span80 Formulation

TABLE I

| | The materials used | | | | |
|---|---|---|---|---|---|
| Polymers & Materials | Abbreviation[a] | Mean mucoadhesive force | % Molecular weight | Melting point | Company |
| Sodium carboxymethyl cellulose | SCMC | 192.4 ± 12.0 | 90,000 | | Aldrich |
| Carbopol ETD 2001 Resin | CP | 185.0 ± 10.3 | | | Goodrich |
| Tragacanth | TC | 154.4 ± 7.5 | | | Aldrich |
| Poly (ethylene oxide) | PEO | 128.6 ± 4.0 | 100,000 | | Aldrich |
| Methylcellulose | MC | 128.0 ± 2.4 | 40,000 | | Aldrich |
| Hydroxypropylmethylcellulose | HPMC | 125.2 ± 16.7 | | | Aldrich |
| Karya gum | KG | 125.2 ± 4.8 | | | Aldrich |
| Cellulose | C | — | | | Aldrich |
| Soluble starch | STRC | 117.2 ± 3.1 | | | Aldrich |
| Gelatin | GT | 115.8 ± 5.6 | | | Aldrich |
| Poly (vinyl pyrrolidone) | PVP | 97.6 ± 3.9 | 55,000 | | Aldrich |
| Poly (ethylene glycol) 8000 | PEG8 | 96.0 ± 7.6 | 8,000 | | Aldrich |
| Poly (ethylene glycol) 4000 | PEG4 | — | 4,000 | | Aldrich |
| Poly (vinyl alcohol) | PVA | 94.8 ± 4.4 | 89,000 ~ 98,000 | | Aldrich |
| Poly (hydroxyethylmethacrylate) | PHEMA | 88.4 ± 2.3 | 300,000 | | Aldrich |

TABLE I-continued

The materials used

| Polymers & Materials | Abbreviation[a] | Mean mucoadhesive force | % Molecular weight | Melting point | Company |
|---|---|---|---|---|---|
| Hydroxypropylcellulose | HPC | 87.1 ± 13.3 | 370,000 | | Aldrich |
| Microcrystalline wax | MCWX | — | | | Dentsply |
| Benzocaine | BZ | — | | 165.2 | Aldrich |
| Span 80 | SP80 | — | | | SIGMA |

[a]Abbreviation was used as a matrix name

Matrix Preparation

The drug and surfactant were physically dispersed into a molten wax matrix. The percentage of polymer, microcrystalline wax (MCWX), Span 80 (SP80), benzocaine (BZ) mixtures was 7.1, 70.9, 2.0, 20.0 respectively. The ratio of polymer to MCWX was fixed as 1: 10. The hydrophilic polymer-wax-surfactant-drug mixtures were prepared by melting microcrystalline wax to approximately 65–70° C. Benzocaine, after passing through a 100-mesh screen by sieve shaker (Vibratory 3-IN, Sieve Shaker, SS-5, Gilson Co.), was added in small portions while the mass was mixed for 5 to 10 minutes. Slowly, the entire mass was then solidified in a vessel with constant mixing. The mixture was allowed to cool down to room temperature. This method was selected because it produced a more uniform matrix than other methods. After one day after, the mass was compressed into 100 mg cores using 9.5 mm punches and die using a pressure of 1,000 lbs. The upper punch was flat and the lower punch was concave. These compressed waxes were used in the Loss of Weight experiments.

Dissolution Procedure

The USP rotating-basket method was employed for investigating drug release from the matrices. A matrix was attached on the flat shaft with the basket, which was immersed in 500 ml of water which was degassed, simulated saliva. The basket was rotated at 60 rpm, and the water bath of the dissolution apparatus (Vander Kamp® 600 Six-spindle Dissolution tester, Van-Kel Inc., USA) was maintained at 37° C. for 8 hrs. Samples were drawn at 0, 5, 10, 15, 20, 30, 60, 90, 120, 180, 240, 300, 360, 420, 480, minutes. At each interval, a 3 ml sample was withdrawn from the vessel for assay, and immediately replaced with an equivalent volume of dissolution medium. Three runs were made on each batch. The samples obtained through 30 minutes were used to calculate the zero-order release rate (Rr).

Benzocaine Assay

The dissolution medium was degassed distilled water. Samples obtained from the dissolution apparatus were diluted with distilled water and assayed for benzocaine content by measuring absorbance at 284.6 nm with UV/VIS spectrophotometer (U-2000 Spectrophotometer, Hitachi, Japan). The concentration in the sample was calculated from a standard Beer's law plot.

Example 2

Release of Benzocaine from Formulation of Varying Polymer Constituents

This study shows the physical properties of the wax/polymer/span80 matrix. The thermal properties were measured. The results of thermal analysis, loss of weight, release rate for 30 minutes, cumulative released percentage amount for 8 hours and the degree of erosion after 8 hours during the dissolution test are given.

Thermal Analysis: A differential scanning calorimeter (DSC 7, differential scanning calorimeter, Perkin-Elmer, USA) was used to determine the energy changes. The samples were placed in aluminum pans and scanned from 10 to 100° C. at 5° C./min. The flow rate of helium gas to purge was 30 cc/min and thermograms were recorded. Three runs for each material were performed.

Loss of Weight Test (L/W): Before the dissolution tests were conducted, a study was conducted to determine the stickiness of the matrix, i.e., how easily it might be removed from surface like a tooth or orthodontic bracket. A 100 mg matrix was compressed as described above except that a piece of waxed weighing paper was placed over the edge of each punch. The matrix was placed into an empty jacketed beaker for 5 min at 37° C., and then immediately, the flat side of the matrix was attached to a glass plate with two sided adhesive tape. After 2 min, the wax paper (cover) on the concave side of the matrix was peeled off by forceps over a 20 second period. The detached wax paper was weighed with the balance (Mettler, Type H6, No. 28088, Metler Instrument Co., Switzerland) and the amount of weight lost by the matrix was recorded. This was repeated for six samples of each formulation.

Erosion After 8 hours (E8) During Release Test: The erosion of the matrices after 8 hours of the release test was recorded by visual observation.

Determination of Matrix Homogeneity: The homogeneity of the matrices was determined by comparing DSC thermograms and by measuring the concentration of benzocaine in various samples. For UV assay, a 100 mg sample was dissolved in 5 mL chloroform. After filtering with polytetrafluoroethylene (PTFE) filtrater (0.45 um Polytetrafluoroethylene sterile syringe filters 13 mm, Altech Associates, Inc.), the sample was assayed in a UV/VIS spectrophotometer as previously described.

Table II lists the results of the various measurements described above including the release rate of benzocaine over the first 30 minutes (Rr0.5), the cumulative amount released over 8 hrs (Ar8), the plateau time ($H_{plateau}$), the erosion condition after 8 hrs (E8), and the loss of weight (L/W) test indicative of matrix stickiness. This table also includes data obtained from thermal analysis of the formulations including the points at which the matrix began to melt and was completely melted (Timp/mp), and the melting point of benzocaine in the matrix (Tbz).

TABLE II

Experimental levels of the experimental variables and values of the seven measured responses for the prepared formulations of polymer/wax matrices

| Formula | Rr 0.5 (%/min) Mean | Ar8 (%) Mean ± SD | Hplateau (hour) | E8[a] | L/W (%) Mean ± SD | Timp/mp (° C.) Mean | Tbz (° C.) Mean |
|---|---|---|---|---|---|---|---|
| SCMC | 0.06 | 13.5 ± 1.3 | >8 | + | 1.12 ± 0.59 | 26/49 | 81 |
| CP | 0.03 | 9.8 ± 1.3 | >8 | + | 0.17 ± 0.12 | 27/50 | 83 |
| TC | 0.13 | 22.7 ± 1.8 | >8 | +++ | 0.35 ± 0.08 | 27/50 | 81 |
| PEO | 0.05 | 10.4 ± 1.5 | >8 | + | 0.53 ± 0.34 | 27/34/50 | 83 |
| MC | 0.05 | 9.6 ± 0.4 | >8 | + | 0.25 ± 0.08 | 28/49 | 82 |
| HPMC | 0.04 | 7.3 ± 0.2 | >8 | + | 0.70 ± 0.23 | 27/51 | 83 |
| KG | 0.05 | 7.0 ± 0.5 | >8 | + | 0.42 ± 0.10 | 28/49 | 79 |
| C | 0.05 | 5.7 ± 0.3 | >8 | + | 0.25 ± 0.15 | 28/50 | 82 |
| STRC | 0.05 | 7.2 ± 0.8 | >8 | + | 1.33 ± 0.59 | 27/51 | 83 |
| GT | 0.05 | 7.1 ± 0.3 | >8 | + | 0.40 ± 0.09 | 27/49 | 81 |
| PVP | 0.03 | 6.2 ± 0.1 | >8 | ++ | 0.15 ± 0.05 | 27/50 | 79 |
| PEG8 | 0.05 | 7.6 ± 0.9 | >8 | + | 0.25 ± 0.18 | 27/50 | 85 |
| PEG4 | 0.07 | 9.3 ± 0.5 | >8 | + | 4.90 ± 2.46 | 27/49 | 81 |
| PVA | 0.04 | 6.6 ± 0.2 | >8 | + | 0.27 ± 0.21 | 27/49 | 82 |
| PHEMA | 0.04 | 6.2 ± 0.3 | >8 | + | 0.50 ± 0.14 | 27/49 | 82 |
| HPC | 0.07 | 8.4 ± 0.2 | >8 | + | 0.48 ± 0.10 | 27/49 | 84 |
| MCWX | 0.04 | 6.5 ± 0.3 | >8 | — | 0.80 ± 0.55 | 26/50 | 85 |
| CNTRL | 1.24 | 85.5 ± 2.5[b] | 4 | ++++ | — | — | — |
| Pure wax | —[c] | — | — | — | — | 24/50 | — |
| Bz | — | — | — | — | — | — | 88 |

[a]+; Not eroded, kept it's shape.
++; sligltly eroded.
+++; eroded.
++++; completely eroded.
[b]After 4 hours
[c]Not measured The cumulative amounts of benzocaine released during the 8 hour dissolution test are presented in Table III.

TABLE III

Percent cumulative release (%) of benzocaine from matrices containing various hydrophilic polymers and span 80

| Formula | Time min | | | | | | | | | | | | |
|---|---|---|---|---|---|---|---|---|---|---|---|---|---|
| | 10 | 20 | 30 | 40 | 60 | 90 | 120 | 180 | 240 | 300 | 360 | 420 | 480 |
| SCMC | 1.3 | 1.9 | 2.4 | 2.9 | 3.7 | 4.6 | 5.7 | 7.4 | 8.9 | 10.0 | 11.4 | 12.7 | 13.5 |
| CP | 1.0 | 1.3 | 1.8 | 1.9 | 2.4 | 2.9 | 3.4 | 4.3 | 5.1 | 6.1 | 7.0 | 8.3 | 9.8 |
| TC | 1.7 | 3.0 | 4.4 | 5.1 | 6.8 | 8.3 | 9.6 | 12.1 | 14.2 | 16.1 | 18.6 | 21.0 | 22.7 |
| PEO | 1.3 | 1.8 | 2.2 | 2.5 | 3.1 | 3.9 | 4.7 | 5.7 | 6.7 | 7.4 | 8.4 | 9.0 | 9.6 |
| MC | 1.3 | 1.7 | 2.1 | 2.6 | 3.1 | 3.9 | 4.8 | 5.9 | 7.1 | 8.1 | 9.0 | 9.6 | 10.4 |
| HPMC | 1.0 | 1.4 | 1.7 | 2.0 | 2.6 | 3.1 | 3.7 | 4.6 | 5.3 | 5.9 | 6.4 | 6.9 | 7.3 |
| KG | 1.1 | 1.6 | 2.1 | 2.4 | 2.9 | 3.4 | 3.9 | 4.6 | 5.2 | 5.8 | 6.1 | 6.5 | 7.0 |
| C | 1.2 | 1.7 | 2.1 | 2.4 | 2.7 | 3.1 | 3.6 | 4.1 | 4.5 | 4.9 | 5.2 | 5.5 | 5.7 |
| STRC | 1.4 | 2.0 | 2.4 | 2.8 | 3.4 | 4.1 | 4.6 | 5.3 | 5.8 | 6.3 | 6.5 | 6.9 | 7.2 |
| GT | 1.4 | 2.0 | 2.3 | 2.7 | 3.2 | 3.8 | 4.4 | 5.1 | 5.6 | 6.1 | 6.5 | 6.7 | 7.1 |
| PVP | 1.0 | 1.4 | 1.6 | 1.8 | 2.2 | 2.7 | 3.2 | 3.8 | 4.5 | 4.9 | 5.4 | 5.8 | 6.2 |
| PEG8 | 1.2 | 1.8 | 2.2 | 2.5 | 3.0 | 3.7 | 4.2 | 5.0 | 5.7 | 6.3 | 6.7 | 7.2 | 7.6 |
| PEG4 | 2.4 | 2.8 | 3.2 | 3.6 | 4.3 | 4.9 | 5.4 | 6.3 | 7.2 | 7.8 | 8.3 | 8.9 | 9.3 |
| PEG 1.5 | 1.3 | 1.9 | 2.2 | 2.8 | 3.6 | 4.4 | 4.7 | 5.8 | 6.5 | 7.0 | 7.7 | 8.4 | 8.9 |
| PVA | 1.2 | 1.6 | 1.9 | 2.2 | 2.6 | 3.1 | 3.6 | 4.3 | 4.8 | 5.3 | 5.7 | 6.2 | 6.6 |
| PHEMA | 1.3 | 1.7 | 2.0 | 2.3 | 2.7 | 3.2 | 3.7 | 4.3 | 4.8 | 5.2 | 5.5 | 5.9 | 6.2 |
| HPC | 1.2 | 1.7 | 2.2 | 2.6 | 3.4 | 3.7 | 4.5 | 5.6 | 6.2 | 6.6 | 7.2 | 7.8 | 8.4 |
| Blank[2] | 1.3 | 1.7 | 2.0 | 2.4 | 2.8 | 3.3 | 3.7 | 4.3 | 4.7 | 5.3 | 5.7 | 6.0 | 6.5 |
| Control[3] | 32.1 | 42.7 | 50.0 | 57.1 | 64.1 | 70.9 | 75.7 | 82.4 | 85.5 | — | — | — | — |

[1]Abbreviation means that it's polymer is mixed with microcrystalline wax, 2% span 80 and 20% benzocaine.
[2]Without polymer.
[c]Conventional dosage form which is PEG gel contained 20% benzocaine.

Conclusions

The greatest release rate over the first 30 minutes and over an 8 hour period was observed when tragacanth (TC) was employed as the hydrophilic polymer in the matrix (FIGS. 1 and 2). None of the formulations yielded asymptotic values ($H_{plateau}$) in the release tests by eight hours. For comparison, the control formulation (CNTRL), which consisted of 20% benzocaine in a water-soluble PEG matrix, showed a $H_{pla}$- t_eau value of 4 hours. Most of the matrices showed no signs of erosion after 8 hours in the dissolution apparatus; the exception was the matrix containing TC. This was likely related to its high benzocaine release rate.

The Loss of Weight test was conducted to determine if the wax matrix would adhere to a surface (e.g. orthodontic bracket) after peeling or removing the matrix from the surface. From FIG. 3 it can be seen that the greatest loss of weight occurred when poly(ethylene glycol) 4000 (PEG4) was employed as the hydrophilic polymer in the formulation. Thermal analysis using DSC showed only slight differences in the initial and final melting points of the matrices, regardless of which hydrophilic polymer was used, as well as the melting point of benzocaine (FIG. 4). It should be noted that the melting point of benzocaine (88–90° C.) was slightly depressed in all the formulations, although the hydrophilic polymer in the formulation had little effect on this value. The formulation containing PEO exhibited an additional broad peak on the thermogram indicative of a physical interaction between PEO and benzocaine.

A subsequent series of experiments was performed to determine the tragacanth-containing formulation with the optimal properties for this application. The percentages of the four components were varied (tragacanth:wax ratio of 0–0.2; 0–5% Span 80; 10–40% benzocaine), and the resulting release rates were measured. When the benzocaine concentration in the formulation was increased, a marked increase in release rates was observed. Increasing the concentration of Span 80 in the formulation had little effect on benzocaine release as long as the benzocaine concentration was 20% or less. When the ratio of tragacanth to wax was increased from 0.1 to 0.2, an increase in benzocaine release was observed; however, the formulation was observed to erode more rapidly. At tragacanth:wax ratios in excess of 0.2, the erosion was unacceptably high.

Although the present invention has been fully described herein, it is to be noted that various changes and modifications are apparent to those skilled in the art. Such changes and modifications are to be understood as included within the scope of the present invention as defined by the appended claims.

What is claimed is:

1. A formulation useful to relieve discomfort associated with irritation due to orthodontic appliances comprising:
   65 to 75% microcrystalline wax;
   5 to 15% non-ionic polymer;
   15 to 25% topical anesthetic; and
   1 to 5% surfactant.

2. A formulation of claim 1, wherein the ratio of non-ionic polymer to microcrystalline wax is no greater than 0.2.

3. A formulation of claim 2, wherein said topical anesthetic is a solid having a particle size smaller than a 100 mesh screen.

4. A formulation of claim 2, wherein the topical anesthetic is benzocaine.

5. A formulation of claim 4, wherein the non-ionic polymer is tragacanth.

6. A formulation of claim 5, wherein the surfactant is Span80.

7. A formulation of claim 6, wherein, of the total, the tragacanth is 7.1%, the microcrystalline wax is 70.9%, the Span80 is 2.0% and the benzocaine is 20.0%.

8. A method of reducing pain due to mucosal abrasions in a patient in need of such pain reduction, comprising administering a formulation of claim 7.

9. A formulation of claim 1, wherein the topical anesthetic is selected from the group consisting of: benzocaine; lidocaine; novocaine; procaine; butalaine; and dyclonine.

10. A formulation of claim 1, wherein the non-ionic polymer is selected from the group consisting of: sodium carboxymethyl cellulose; Carbopol ETD 2001 resin; tragacanth; poly (ethylene oxide); methylcellulose; hydroxypropylmethylcellulose; karya gum; cellulose; soluble starch; gelatin; poly (vinyl pyrrolidone); poly (ethylene glycol) 8000; poly (ethylene glycol) 4000; and poly (vinyl alcohol).

11. A formulation of claim 1, wherein the surfactant is selected from the group consisting of: sorbitan monolaurate, polysorbate 80, Spans and Tweens.

12. A method of reducing pain due to mucosal abrasions in a patient in need of such pain reduction, comprising administering a formulation of claim 1.

13. A method to prepare a formulation of claim 1, comprising:
   melting the microcrystalline wax using at least one temperature in the range of approximately 65 to 70° C.; and
   adding the non-ionic polymer and the surfactant to said melted microcrystalline wax, with stirring; and
   adding the topical anesthetic with particle size less than the apertures in a 100 mesh screen, with mixing, so as to obtain a homogenous mixture of said anesthetic, wax, polymer and surfactant; and
   cooling said mixture at a constant rate, with continuous agitation, so as to congeal the mixture into a homogeneous matrix.

14. A method of claim 13, wherein the topical anesthetic is selected from the group consisting of: benzocaine; lidocaine; novocaine; procaine; butalaine; and dyclonine.

15. A method of claim 14, wherein the non-ionic polymer is selected from the group consisting of: sodium carboxymethyl cellulose; Carbopol ETD 2001 resin; tragacanth; poly (ethylene oxide); methylcellulose; hydroxypropylmethylcellulose; karya gum; cellulose; soluble starch; gelatin; poly (vinyl pyrrolidone); poly (ethylene glycol) 8000; poly (ethylene glycol) 4000; and poly (vinyl alcohol).

16. A method of claim 15, wherein the surfactant is selected from the group consisting of: sorbitan monolaurate and polysorbate 80.

17. A method of claim 13, wherein the homogeneous matrix is formed into uniform pieces of a size appropriate to place on individual dental brackets.

18. A method of claim 13, wherein the topical anesthetic is benzocaine.

19. A method of claim 18, wherein the non-ionic polymer is tragacanth.

20. A method of claim 19, wherein the surfactant is Span80.

21. A method of claim 20, wherein, of the total, the tragacanth is 7.1%, the microcrystalline wax is 70.9%, the Span80 is 2.0% and the benzocaine is 20.0%.

* * * * *